US009982018B2

(12) United States Patent
Müller et al.

(10) Patent No.: US 9,982,018 B2
(45) Date of Patent: May 29, 2018

(54) AMATOXIN DERIVATIVES

(71) Applicant: HEIDELBERG PHARMA GMBH, Ladenburg (DE)

(72) Inventors: Christoph Müller, Birkenau (DE); Jan Anderl, Modautal (DE); Werner Simon, Hüffelsheim (DE); Christian Lutz, Weinheim (DE); Torsten Hechler, Bensheim (DE)

(73) Assignee: Heidelberg Pharma GmbH, Ladenburg (DE)

( * ) Notice: Subject to any disclaimer, the term of this patent is extended or adjusted under 35 U.S.C. 154(b) by 0 days. days.

(21) Appl. No.: 14/769,970

(22) PCT Filed: Mar. 10, 2014

(86) PCT No.: PCT/EP2014/000614
§ 371 (c)(1),
(2) Date: Aug. 24, 2015

(87) PCT Pub. No.: WO2014/135282
PCT Pub. Date: Sep. 12, 2014

(65) Prior Publication Data

US 2016/0002298 A1 Jan. 7, 2016

(30) Foreign Application Priority Data

Mar. 4, 2013 (EP) .................................... 13001074

(51) Int. Cl.
*C07K 7/64* (2006.01)
*C07K 16/32* (2006.01)
*A61K 47/68* (2017.01)

(52) U.S. Cl.
CPC ............ *C07K 7/64* (2013.01); *A61K 47/6831* (2017.08); *A61K 47/6851* (2017.08); *A61K 47/6855* (2017.08); *C07K 16/32* (2013.01)

(58) Field of Classification Search
None
See application file for complete search history.

(56) References Cited

U.S. PATENT DOCUMENTS

2012/0100161 A1* 4/2012 Faulstich ......... A61K 47/48492 424/183.1

FOREIGN PATENT DOCUMENTS

| | | | |
|---|---|---|---|
| WO | 2007121326 | A2 | 10/2007 |
| WO | 2010115629 | A2 | 10/2010 |
| WO | 2012041504 | A1 | 4/2012 |
| WO | 2012119787 | A1 | 9/2012 |

OTHER PUBLICATIONS

National Center for Biotechnology Information. PubChem Compound Database; CID=676246, https://pubchem.ncbi.nlm.nih.gov/compound/676246 (accessed Mar. 29, 2017).*

Binz et al. (Nature Biotechnology Oct. 2005 23 (10): 1257-1268) (Year: 2005).*

International Search Report and Written Opinion dated Apr. 7, 2014 in PCT/EP2014/000614 (11 pages).

Anderl et al., "Chemical modification allows phallotoxins and amatoxins to be used as tools in cell biology", Beilstein Journal of Organic Chemistry, Nov. 27, 2012, 8:2072-2084.

Salnikov et al., "322 Efficacy of Amanitin Conjugated Chimeric Anti-EpCAM Monoclonal Antibody in Experimental Carcinomas", European Journal of Cancer, Nov. 1, 2012, 48:98-99.

Moldenhauer et al., "Therapeutic Potential of Amanitin-Conjugated Anti-Epithelial Cell Adhesion Molecule Monoclonal Antibody Against Pancreatic Carcinoma", JNCI Journal of the National Cancer Institute, Apr. 18, 2012, 104(8):622-634.

* cited by examiner

*Primary Examiner* — Peter J Reddig
(74) *Attorney, Agent, or Firm* — Prismatic Law Group, PLLC

(57) ABSTRACT

The invention relates to tumor therapy. In one aspect, the present invention relates to conjugates of an amatoxin and a target-binding moiety, e.g. an antibody, connected by certain linkages, which are useful in the treatment of cancer and other disorders and diseases. In a further aspect the invention relates to pharmaceutical compositions comprising such conjugates.

24 Claims, 7 Drawing Sheets

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |

| | Her-30.0643 [4.4] | Her-30.1033 [3.9] | Her-30.1036 [4.0] |
|---|---|---|---|
| EC50 | 2.942e-011 | 2.748e-011 | 3.832e-011 |

| | Her-30.0643 [4.3] | Her-30.1165 [5.0] |
|---|---|---|
| EC50 | 2.713e-011 | 1.081e-010 |

| | Her-30.0643 [4.4] | Her-30.1033 [3.9] | Her-30.1036 [4.0] |
|---|---|---|---|
| EC50 | 1.997e-011 | 1.258e-011 | 3.271e-011 |

| | Her-30.0643 [4.4] | Her-30.1033 [3.9] | Her-30.1036 [4.0] |
|---|---|---|---|
| EC50 | 1.004e-009 | 7.912e-010 | 2.103e-009 |

AMATOXIN DERIVATIVES

CROSS REFERENCE TO RELATED APPLICATIONS

The present invention is filed under 35 U.S.C. § 371 as the U.S. national phase of International Application No. PCT/EP2014/000614, filed Mar. 10, 2014, which designated the U.S. and claims the benefit of priority to European Patent Application No. 13001074.7, filed Mar. 4, 2013, each of which is hereby incorporated in its entirety including all tables, figures and claims.

FIELD OF THE INVENTION

The invention relates to tumour therapy. In one aspect, the present invention relates to conjugates of an amatoxin and a target-binding moiety, e.g. an antibody, connected by certain linkages, which are useful in the treatment of cancer and other disorders and diseases. In a further aspect the invention relates to pharmaceutical compositions comprising such conjugates.

BACKGROUND OF THE INVENTION

Amatoxins are cyclic peptides composed of 8 amino acids. They can, for example, be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 1981, 213, 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res 1983, 21 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji), and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the Amatoxins, were provided.

Patent applications WO 2010/115629 and WO 2010/115630 (both published Oct. 14, 2010) describe conjugates, where antibodies, such as anti-EpCAM antibodies such as humanized huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly of via a linker between the antibody and the amatoxins. The suggested linkers comprise elements such as an ester, an ether, a urethane, a peptide bond and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

Structure activity relationship of amatoxins is reviewed in by Wieland (T. Wieland, Peptides of Poisonous *Amanita* Mushrooms, *Springer series in molecular biology*, Springer Verlag New York, 1986). The hydroxyl group of amino acid 2 (hydroxy proline) and the γ-hydroxy group of amino acid 3 (dihydroxy-isoleucine) are assumed as essential for activity, whereas the functionalities at amino acid 1 (aspartate or asparagine), amino acid 4 (6-hydroxy-tryptophan) and the 8-hydroxy-group at amino acid 3 are more tolerant for chemical modifications. This indicates that the latter positions are the preferred sites for linker attachment, while modifications of the first ones should be avoided.

It is known that amatoxins are relatively non-toxic when coupled to large biomolecule carriers, such as antibody molecules, and that they exert their cytotoxic activity only after the biomolecule carrier is cleaved off. In light of the toxicity of amatoxins, particularly for liver cells, it is of outmost importance that amatoxin conjugates for targeted tumour therapy remain highly stable after administration in plasma, and that the release of the amatoxin occurs after internalization in the target cells. In this context, minor improvements of the conjugate stability may have drastic consequences for the therapeutic window and the safety of the amatoxin conjugates for therapeutic approaches.

OBJECTS OF THE INVENTION

It was an object of the present invention to provide further target-binding moiety amatoxin conjugates that are stable in plasma, so that harmful side effects to non-target cells are minimized.

SUMMARY OF THE INVENTION

The present invention is based on the unexpected observation that a ring formation via the two oxygen atoms bound to the γ and the δ C atoms of amatoxin amino acid 3 can improve the tolerability of target-binding moiety amatoxin conjugates without interfering with the interaction of such amatoxins with their target, the DNA-dependent RNA polymerase II of mammalian cells. To date, the presence of the hydroxyl group bound to the γ C atom of amatoxin amino acid 3 has been considered essential for the efficacy of amatoxins and amatoxin conjugates. Wieland (T. Wieland, Peptides of Poisonous *Amanita* Mushrooms, Springer Series in Molecular Biology, Springer Verlag New York, 1986; Wieland T, Rempel D, Gebert U, Buku A, Boehringer H. Über die Inhaltsstoffe des grünen Knollenblätterpilzes. XXXII. Chromatographische Auftrennung der Gesamtgifte und Isolierung der neuen Nebentoxine Amanin und Phallisin sowie des ungiftigen Amanullins. Liebigs Ann Chem. 1967; 704:226-236) reports for naturally occurring amatoxins like amanullin that lacks the γ-hydroxyl group a considerably reduced toxicity.

In a first aspect, the present invention relates to an amatoxin of Formula I

I

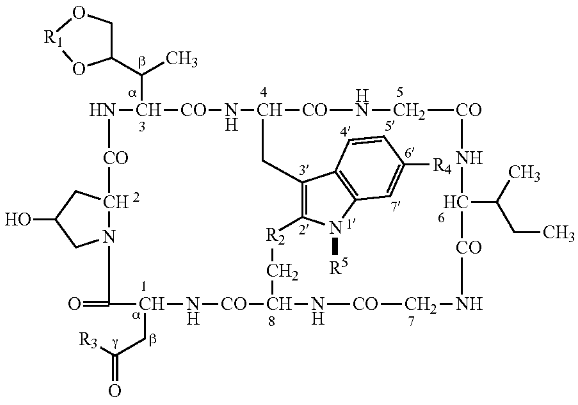

wherein:

$R^1$ is selected from C═O, C═S, C═$NR^6$ and $CR^7R^8$;

$R^2$ is selected from S═O, $SO_2$ and S;

$R^3$ is selected from $NHR^5$ and $OR^5$;

$R^4$ is selected from H, $OR^5$, and $OC_{1-6}$-alkyl;

$R^6$ is selected from $C_{1-6}$-alkylene-$R^5$, cycloalkylene-$R^5$, heterocycloalkylene-$R^5$, arylene-$R^5$, and heteroarylene-$R^5$;

$R^7$ and $R^8$ are independently selected from H, $C_{1-6}$-alkylene-$R^5$, cycloalkylene-$R^5$, heterocycloalkylene-$R^5$, arylene-$R^5$, and heteroarylene-$R^5$;

wherein:

(i) each $R^5$ is H;

(ii) one of $R^5$ is -$L_n$-X, wherein L is a linker, n is selected from 0 and 1, and X is a chemical moiety that can be coupled with a targeting moiety, and wherein the remaining $R^5$ are H; or (iii) one of $R^5$ is -$L_n$-X*—Y, wherein L is a linker, n is selected from 0 and 1, Y is a targeting moiety, and X* is a chemical moiety resulting from coupling X with a functional group of Y, and wherein the remaining $R^5$ are H.

In another aspect the present invention relates to an amatoxin of the present invention for use as a medicament.

In another aspect the present invention relates to an amatoxin of the present invention for use in the treatment of cancer in a patient, particularly wherein the cancer is selected from the group consisting of breast cancer, gastrointestinal cancers, e.g. colorectal cancer, pancreatic cancer, cholangiocarcinoma, hepatocellular carcinoma, osteosarcoma, lung cancer, prostate cancer, squamous cell carcinoma, ovarian cancer, testis carcinoma, bladder carcinoma, stomach cancer, head and neck cancer, cervix carcinoma, kidney cancer, gliomas, skin cancer, e.g. malignant melanoma, thyroid cancer, leukemia, and malignant lymphoma.

In another aspect the present invention relates to pharmaceutical composition comprising the amatoxin according to the present invention and further comprising one or more pharmaceutically acceptable diluents, carriers, excipients, fillers, binders, lubricants, glidants, disintegrants, adsorbents; and/or preservatives.

In another aspect the present invention relates to a method for synthesizing the amatoxin of the present invention, comprising the step of reacting an amatoxin of formula II

II

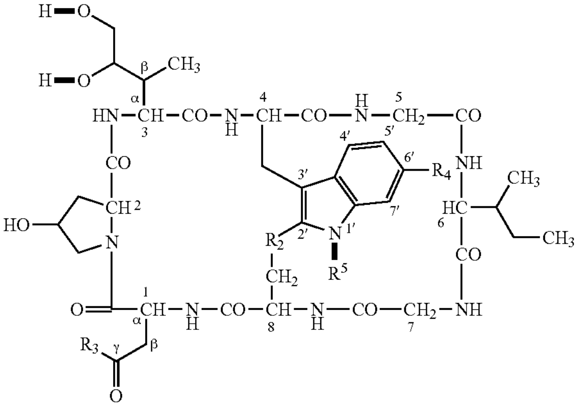

wherein:

$R^2$ is selected from S═O, $SO_2$, and S;

$R^3$ is selected from $NHR^5$ and $OR^5$;

$R^4$ is selected from H, $OR^5$, and $OC_{1-5}$-alkyl;

$R^6$ is selected from $C_{1-6}$-alkylene-$R^5$, cycloalkylene-$R^5$, heterocycloalkylene-$R^5$, arylene-$R^5$, and heteroarylene-$R^5$;

$R^7$ and $R^8$ are independently selected from H, $C_{1-6}$-alkylene-$R^5$, cycloalkylene-$R^5$, heterocycloalkylene-$R^5$, arylene-$R^5$, and heteroarylene-$R^5$;

wherein one of $R^5$ is -$L_n$-X, wherein L is a linker, n is selected from 0 and 1, and X is a chemical moiety that can be coupled with a targeting moiety, and wherein the remaining $R^5$ are H;

with (i) N,N'-disuccinimidyl carbonate (DSC), (ii) a thiocarbonylating reagent, particularly thiophosgene, 1,1'-thiocarbonyldiimidazole or 1,1'-thiocarbonyldi-2(1H)-pyridone; (iii) an iminocarbonylating reagent, particularly an isocyanide dichloride or phenylisotihocyanate; or (iv) an aldehyde, ketone or acyclic acetal.

DETAILED DESCRIPTION OF THE INVENTION

Figure 1:
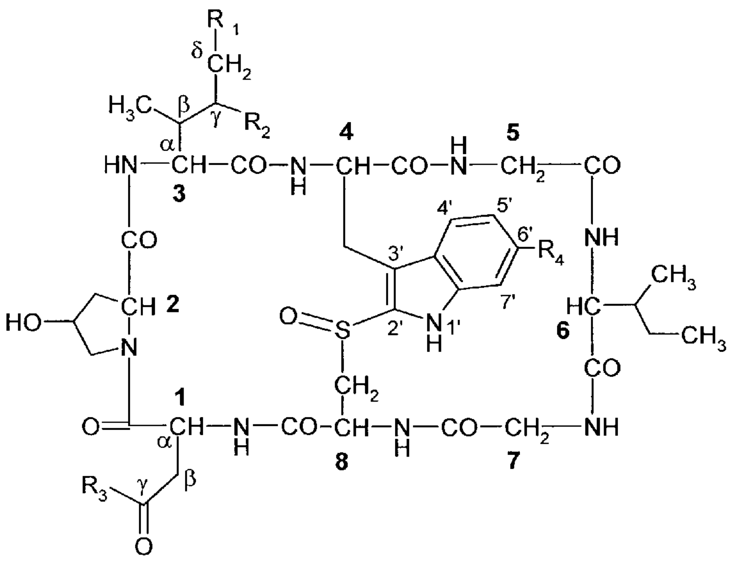
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).
Figure 2:
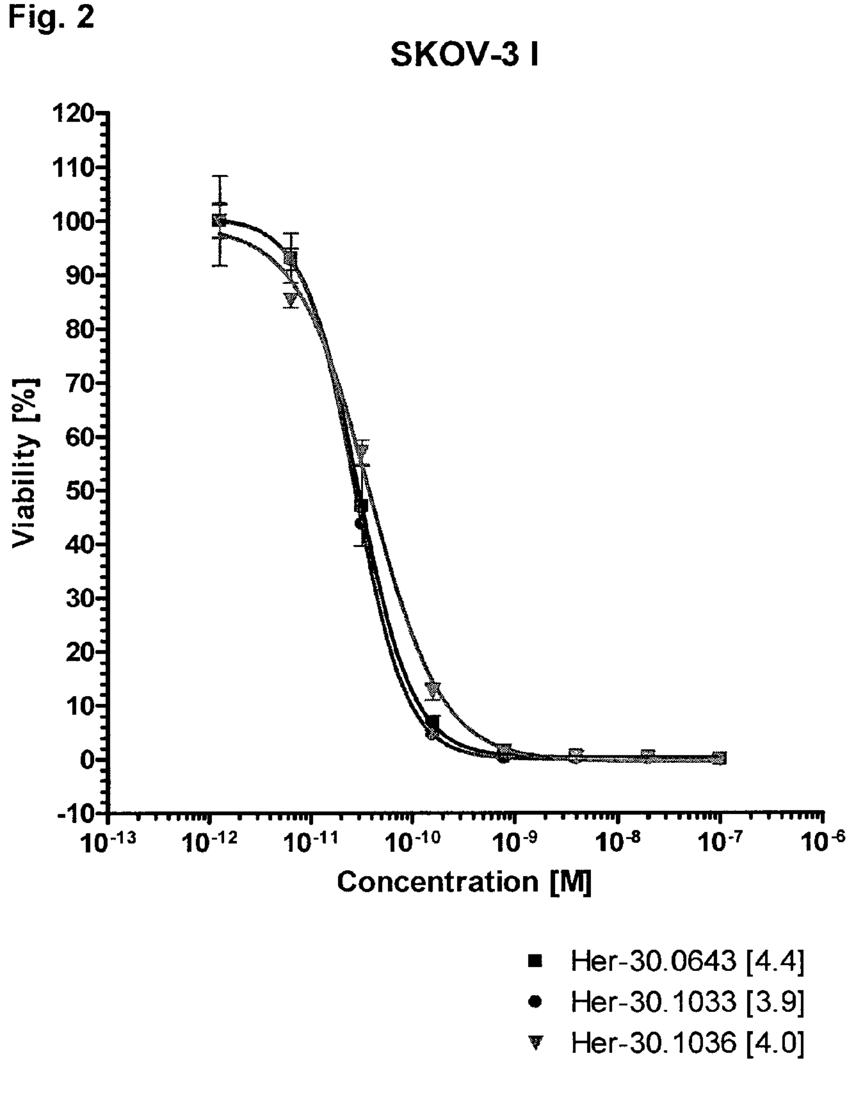
FIG. 2 shows the cytotoxic activity of different amatoxin Trastuzumab (trade name Herceptin®) conjugates on SK-OV-3 (ovarian cancer) cells in a BrdU assay after incubation for 72 h.
Figure 3:
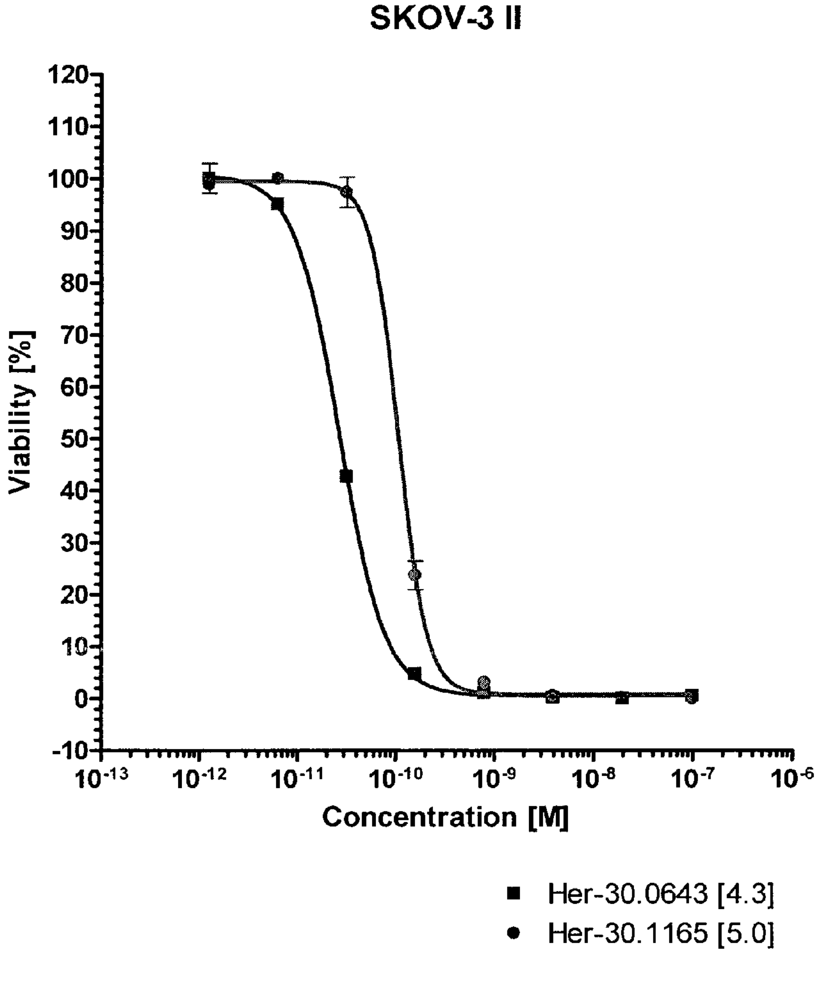
FIG. 3 shows the cytotoxic activity of different amatoxin-Trastuzumab conjugates on SK-OV-3 (ovarian cancer) cells in a BrdU assay after incubation for 72 h.
Figure 4:
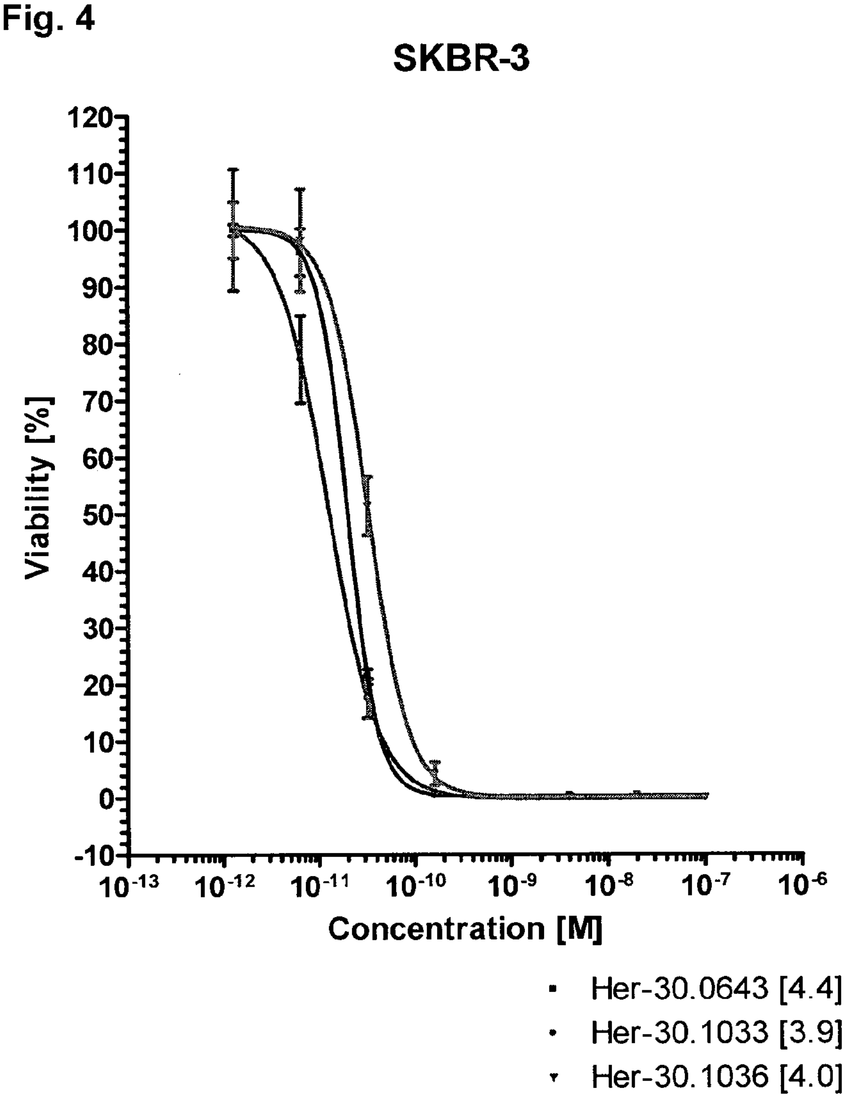
FIG. 4 shows the cytotoxic activity of different amatoxin amatoxin-Trastuzumab conjugates on SKBR-3 (breast cancer) cells in a BrdU assay after incubation for 72 h.
Figure 5:
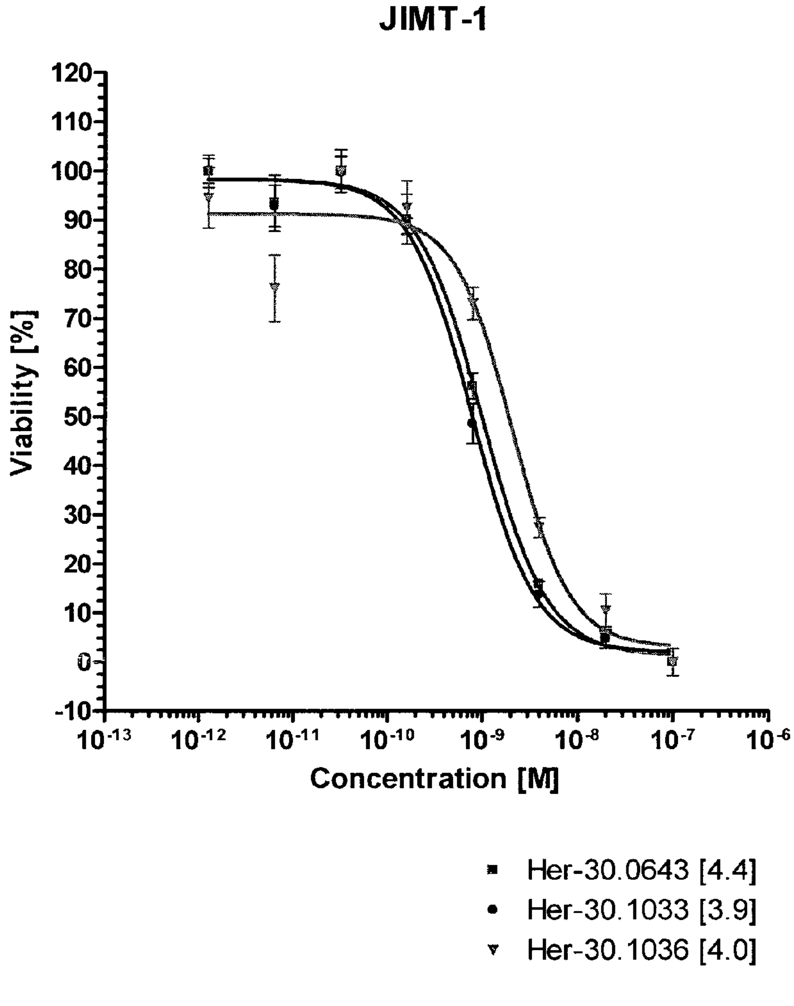
FIG. 5 shows the cytotoxic activity of different amatoxin amatoxin-Trastuzumab conjugates on JIMT-1 (breast cancer) cells in a BrdU assay after incubation for 72 h.

The present invention may be understood more readily by reference to the following detailed description of the invention and the examples included therein.

In a first aspect, the present invention relates to an amatoxin of formula I

I

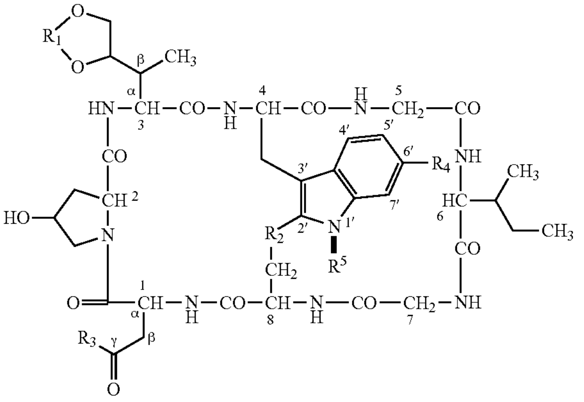

wherein:

$R^1$ is selected from C═O, C═S, C═$NR^6$ and $CR^7R^8$;

$R^2$ is selected from S═O, $SO_2$, and S;

$R^3$ is selected from $NHR^5$ and $OR^5$;

$R^4$ is selected from H, $OR^5$, and $OC_{1-6}$-alkyl;

$R^6$ is selected from $C_{1-6}$-alkylene-$R^5$, cycloalkylene-$R^5$, heterocycloalkylene-$R^5$, arylene-$R^5$, and heteroarylene-$R^5$;

$R^7$ and $R^8$ are independently selected from H, $C_{1-6}$-alkylene-$R^5$, cycloalkylene-$R^5$, heterocycloalkylene-$R^5$, arylene-$R^5$, and heteroarylene-$R^5$;

wherein:

(i) each $R^5$ is H;

(ii) one of $R^5$ is -$L_n$-X, wherein L is a linker, n is selected from 0 and 1, and X is a chemical moiety that can be coupled with a targeting moiety, and wherein the remaining $R^5$ are H; or (iii) one of $R^5$ is -$L_n$-X*—Y, wherein Lisa linker, n is selected from 0 and 1, Y is a targeting moiety, and X* is a chemical moiety resulting from coupling X with a functional group of Y, and wherein the remaining $R^5$ are H.

The term “target-binding moiety”, as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. “Target-binding moieties” suitable for use in the present invention typically have a molecular mass of 40 000 Da (40 kDa) or more.

As used herein, a first compound (e.g. an antibody) is considered to “specifically bind” to a second compound (e.g. an antigen, such as a target protein), if it has a dissociation constant $K_D$ to said second compound of 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

In the context of the present application the terms “target molecule” and “target epitope”, respectively, refers to an antigen and an epitope of an antigen, respectively, that is specifically bound by a target-binding moiety. Preferably the target molecule is a tumour-associated antigen, in particular an antigen or an epitope which is present on the surface of one or more tumour cell types or tumour-associated cells in an increased concentration and/or in a different steric configuration as compared to the surface of non-tumour cells. Preferably, said antigen or epitope is present on the surface of one or more tumour or tumour stroma cell types, but not on the surface of non-tumour cells. In particular embodiments, the target-binding moiety specifically binds to an epitope of HER-2/neu or epithelial cell adhesion molecule (EpCAM). In other embodiments, said antigen or epitope is preferentially expressed on cells involved in autoimmune diseases. In particular such embodiments, the target-binding moiety specifically binds to an epitope of the IL-6 receptor (IL-6R). In other embodiments, said antigen or epitope is preferentially expressed on cells involved in an inflammatory disease.

The term “antibody or antigen binding fragment thereof”, as used herein, refers to immunoglobulin molecules and immunologically active portions of immunoglobulin molecules, i.e. molecules that contain an antigen binding site that immunospecifically binds an antigen. Also comprised are immunoglobulin-like proteins that are selected through techniques including, for example, phage display to specifically bind to a target molecule, e.g. to the target protein Her-2/neu or EpCAM. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. “Antibodies and antigen-binding fragments thereof” suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, $F(ab')_2$ fragments, fragments produced by a Fab expression library, diabodies or tetrabodies (Holliger P. et al., 1993), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and $F(ab')_2$, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Preferably, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz et al. 2005). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, 2000). The nucleic acid aptamer may be a DNA or RNA molecule. The aptamers may contain modifications, e.g. modified nucleotides such as 2'-fluorine-substituted pyrimidines.

As used herein, an "aptamer conjugate" refers to a target-binding moiety toxin conjugate in which the target-binding moiety is a nucleic acid aptamer according to above alternative (iii).

A "linker" in the context of the present invention refers to a molecule that is connecting two components, each being attached to one end of the linker, and which increases the distance between two components and alleviates steric interference between these components, such as in the present case between the target-binding moiety and the amatoxin. In the absence of a linker, a direct linkage of amatoxin to the target-binding moiety may decrease the ability of the amatoxin to interact with RNA polymerase II. In particular embodiments, a linker has a continuous chains of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the amatoxin moiety and the target-binding moiety, wherein one side of the linker backbone has been reacted with the amatoxin and, the other side with a target-binding moiety. In the context of the present invention, a linker preferably is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times.

In some embodiments the linker may comprise a disulfide bond. It is understood that the linker has to be attached either in a single step or in two or more subsequent steps to the amatoxin and the target-binding moiety. To that end the linker to be will carry two groups, preferably at a proximal and distal end, which can (i) form a covalent bond to a group present in one of the components to be linked, preferably an activated group on an amatoxin or the target binding-peptide or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In the context of the present invention, the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 1978 December; 5(3):185-260), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in which the thioether sulfoxide moiety is replaced by a sulfide, sulfone, or by atoms different from sulfur, e.g. a carbon atom as in a carba-analogue of amanitin, in each case wherein any such derivative or analogue is functionally active by inhibiting mammalian RNA polymerase II.

As used herein, a "chemical derivative" (or short: a "derivative") of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

As used herein, an "analogue" of a compound is structurally related but not identical to the compound and exhibits at least one activity of the compound. The compound to which the analogue is compared is known as the "parent" compound. The afore-mentioned activities include, without limitation: binding activity to another compound; inhibitory activity, e.g. enzyme inhibitory activity; toxic effects; activating activity, e.g. enzyme-activating activity. It is not required that the analogue exhibits such an activity to the same extent as the parent compound. A compound is regarded as an analogue within the context of the present application, if it exhibits the relevant activity to a degree of at least 1% (more preferably at least 5%, more preferably at least 10%, more preferably at least 20%, more preferably at least 30%, more preferably at least 40%, and more preferably at least 50%) of the activity of the parent compound. Thus, an "analogue of an amatoxin", as it is used herein, refers to a compound that is structurally related to any one of α-amanitin, β-amanitin, γ-amanitin, ε-amanitin, amanin, amaninamide, amanullin, and amanullinic acid as shown in FIG. 1 and that exhibits at least 1% (more preferably at least 5%, more preferably at least 10%, more preferably at least 20%, more preferably at least 30%, more preferably at least 40%, and more preferably at least 50%) of the inhibitory activity against mammalian RNA polymerase II as compared to at least one of α-amanitin, β-amanitin, γ-amanitin, ε-amanitin, amanin, amaninamide, amanullin, and amanullinic acid. An "analogue of an amatoxin" suitable for use in the present invention may even exhibit a greater inhibitory activity against mammalian RNA polymerase II than any one of α-amanitin, β-amanitin, γ-amanitin, ε-amanitin, amanin, amaninamide, amanullin, or amanullinic acid.

The inhibitory activity might be measured by determining the concentration at which 50% inhibition occurs ($IC_{50}$ value). The inhibitory activity against mammalian RNA polymerase II can be determined indirectly by measuring the inhibitory activity on cell proliferation. A suitable assay for measuring inhibition of cell proliferation is described in the examples.

A "semisynthetic analogue" refers to an analogue that has been obtained by chemical synthesis using compounds from natural sources (e.g. plant materials, bacterial cultures, fungal cultures or cell cultures) as starting material. Typically, a "semisynthetic analogue" of the present invention has been synthesized starting from a compound isolated from a mushroom of the Amanitaceae family. In contrast, a "synthetic analogue" refers to an analogue synthesized by so-called total synthesis from small (typically petrochemical) building blocks. Usually, this total synthesis is carried out without the aid of biological processes.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin, and amanullinic acid as shown in FIG. 1 as well as salts, chemical derivatives, semisynthetic analogues, and synthetic analogues thereof. Particularly preferred amatoxins for use in the present invention are α-amanitin, β-amanitin, and amaninamide.

In a particular embodiment of the present invention, the amatoxin of (iii), wherein the functional group of Y of the amatoxin of (iii) is an amino group.

In a particular such embodiment, X* is a urea moiety.

In a particular embodiment of the present invention, said residue $R^5$ being $-L_a$-X*—Y is:

(i) present in $R^1$;

(ii) present in $R^3$;

(iii) present in $R^4$; or (iv) present in $R^5$.

In a particular embodiment of the present invention, said amatoxin is selected from α-amanitin, β-amanitin, amanin, amaninamide, or from salts or analogues thereof.

In particular embodiments, the linker L of (ii) or (iii) is a linear chain of between 1 and 20 atoms independently selected from C, O, N and S, particularly between 2 and 16 atoms, more particularly between 5 and 14 atoms, and even more particularly between 6 and 12 atoms. In particular embodiments, at least 60% of the atoms in the linear chain are C atoms. In particular embodiments, the atoms in the linear chain are linked by single bonds.

In particular embodiments. the linker of (ii) or (iii) has a length of up to 12 atoms, particularly from 2 to 10, more particularly from 4 to 9, and most particularly from 6 to 8 atoms.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($—CH_2—$), ethylene ($—CH_2—CH_2—$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene (—CH═CH—), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. ═O) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, inclucing perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, arylthio)ureido, alkyl(thio)ureido, cycloalkyl(thio)ureido, aryloxy, aralkoxy, or $—O(CH_2)_n—OH$, $—O(CH_2)_n—NH_2$, $—O(CH_2)_nCOOH$, $—(CH_2)_nCOOH$, $—C(O)O(CH_2)_nR$, $—(CH_2O(H)C(O)OR$, or $—N(R)S(O)_2R$ wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(═O)— or —C(═O)—O—), a carboxamide (—NH—C(═O)— or —C(═O)—NH—), a urethane (—NH—C(═O)—O— or —O—C(═O)—NH—), and a urea moiety (—NH—C(═O)—NH—).

In particular embodiments of the present invention, the linker L of (ii) or (iii) comprises m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises n moiety independently selected from one of the following moieties: a disulfide (—S—S—), an ether (—O—), a thioether (—S—), an amine (—NH—), an ester (—O—C(═O)— or —C(═O)—O—), a carboxamide (—NH—C(═O)— or —C(═O)—NH—), a urethane (—NH—C(═O)—O— or —O—C(═O)—NH—), and a urea moiety (—NH—C(═O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In particular embodiments, the C atoms in the linear chain are independently part of optionally substituted methylene groups ($—CH_2—$). In particular such embodiments, the optional substituents are independently selected from halogen and $C_{1-6}$-alkyl, particularly methyl.

In particular embodiments, the linker L, particularly the linker L as shown in section[0043], is selected from the following group of linkers:

amatoxin side: $—(CH_2)_2—$ target-binding moiety side;
amatoxin side: $—(CH_2)_3—$ target-binding moiety side;
amatoxin side: $—(CH_2)_4—$ target-binding moiety side;
amatoxin side: $—(CH_2)_5—$ target-binding moiety side;
amatoxin side: $—(CH_2)_6—$ target-binding moiety side;
amatoxin side: $—(CH_2)_7—$ target-binding moiety side;
amatoxin side: $—(CH_2)_8—$ target-binding moiety side;
amatoxin side: $—(CH_2)_9—$ target-binding moiety side;
amatoxin side: $—(CH_2)_{10}—$ target-binding moiety side;
amatoxin side: $—(CH_2)_{11}—$ target-binding moiety side;
amatoxin side: $—(CH_2)_{12}—$ target-binding moiety side;
amatoxin side: $—(CH_2)_{16}—$ target-binding moiety side;
amatoxin side: $—(CH_2)_2—S—S—(CH_2)_2—$ target-binding moiety side;
amatoxin side: $—(CH_2)_3—S—S—(CH_2)_2—$ target-binding moiety side;
amatoxin side: $—(CH_2)_2—S—S—(CH_2)_3—$ target-binding moiety side;
amatoxin side: $—(CH_2)_3—S—S—(CH_2)_3—$ target-binding moiety side;
amatoxin side: $—(CH_2)_4—S—S—(CH_2)_4—$ target-binding moiety side;
amatoxin side: $—(CH_2)_2—CMe_2\text{-}S—S—(CH_2)_2—$ target-binding moiety side;
amatoxin side: $—(CH_2)_2—S—S—CMe_2\text{-}(CH_2)_2—$ target-binding moiety side;
amatoxin side: $—(CH_2)_2—O—(CH_2)_2—$ target-binding moiety side;
amatoxin side: $—(CH_2)_2—O—(CH_2)_2—O—(CH_2)_2—$ target-binding moiety side;
amatoxin side: $—(CH_2)_2—O—(CH_2)_2—O—(CH_2)_2—O—(CH_2)_2—$ target-binding moiety side;
amatoxin side: $—(CH_2)_2—O—(CH_2)_2—O—(CH_2)_2—O—(CH_2)_2—O—(CH_2)_2—$ target-binding moiety side;
amatoxin side: $—CH_2—C_6H_4—$NH-Cit-Val-$(CH_2)_6—$ target-binding moiety side;
amatoxin side: $—CH_2—C_6H_4—$NH-Lys-Phe-$(CH_2)_6—$ target-binding moiety side;
amatoxin side: $—CH_2—C_6H_4—$NH-Val-Val-$(CH_2)_6—$ target-binding moiety side;
amatoxin side: $—CH_2—C_6H_4—$NH-Ile-Val-$(CH_2)_6—$ target-binding moiety side;
amatoxin side: $—CH_2—C_6H_4—$NH-His-Val-$(CH_2)_6—$ target-binding moiety side;
amatoxin side: $—CH_2—C_6H_4—$NH-Met-Val-$(CH_2)_6—$ target-binding moiety side; and
amatoxin side: $—CH_2—C_6H_4—$NH-Asn-Lys-$(CH_2)_6—$ target-binding moiety side.

In particular embodiments, the target-binding moiety specifically binds to an epitope that is present on a tumour cell, particularly wherein the target-binding moiety specifically binds to an epitope of human epidermal growth factor receptor 2 (HER2).

In particular embodiments, the antibody is Trastuzumab or HEA125, or an antibody fragment comprising the antigen binding fragment of Trastuzumab or HEA125.

In particular embodiments, more than one amatoxin molecule is coupled to one target-binding moiety An increase of the number of amatoxins per conjugate will also increase the toxicity. Accordingly, in a particular embodiment the ratio of target-binding moiety to amatoxin is between 1 target-binding moiety to between 1 and 15 amatoxin molecules, particularly 1, 2, 3, 4, 5, 6, 7, 8, 9, 10, 11, 12, 13, 14, or 15. For the purpose of the calculation of the ratio in case of antibody dimers such as IgGs, the dimer is considered as one target-binding moiety.

In particular embodiments. the target-binding moiety is selected from the group consisting of:

(i) antibody or antigen-binding fragment thereof;
(ii) antibody-like protein; and
(iii) nucleic acid aptamer.

In particular embodiments. the the antibody or the antigen-binding fragment thereof is selected from a diabody, a tetrabody, a nanobody, a chimeric antibody, a deimmunized antibody, a humanized antibody or a human antibody.

In particular embodiments. the antigen binding fragment is selected from the group consisting of Fab, $F(ab')_2$, Fd, Fv, single-chain Fv, and disulfide-linked Fvs (dsFv).

In another aspect the present invention relates to an amatoxin of the present invention for use as a medicament.

In another aspect the present invention relates to an amatoxin of the present invention for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma As used herein, a "patient" means any mammal or bird who may benefit from a treatment with the target-binding moiety toxin conjugates described herein. Preferably, a "patient" is selected from the group consisting of laboratory animals (e.g. mouse or rat), domestic animals (including e.g. guinea pig, rabbit, chicken, pig, sheep, goat, camel, cow, horse, donkey, cat, or dog), or primates including human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising the amatoxin according to the present invention and further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The amatoxins of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are preferably aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

In particular embodiments of the present invention, X is a carbamic acid derivative —NH—C(O)—Z, wherein Z is a leaving group that can be replaced by a nucleophilic group of a target-binding moiety, particularly by a primary amine of a target-binding moiety.

In particular embodiments, Z is selected from: -$^t$butyloxy, -succinimidyloxy, -1-O-succinimidyloxy-3-sulfonate (-Sulfo-NHS), —O-(4-nitrophenyloxy), —O-(3-nitrophenyloxy), —O-(2,4-d initrophenyloxy), —O-(2,4-dichloro-6-nitrophenyloxy), -pentafluorophenyloxy, -pentachlorophenyloxy, —O-(2,4,5-trichlorophenyloxy), —O-(3,4-dihydro-3-hydroxy-4-oxo-1,2,3-benzotriazine-3-yl), —O-(endo-1-hydroxy-5-norbornene-2,3-dicarboximide-1-yl), -1-phthalimidoyloxy, -1-benzotriazolyloxy, -1-(7-aza-benzotriazolyl)oxy), and —N-imidazolyl.

In another aspect the present invention relates to a method for synthesizing the amatoxin of the present invention, comprising the step of reacting an amatoxin of Formula II

II

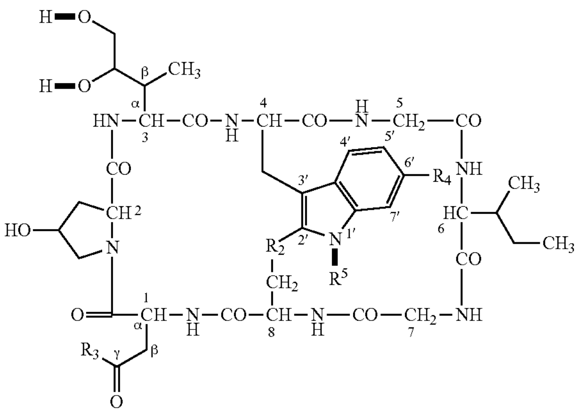

wherein:

$R^2$ is selected from S═O, $SO_2$, and S;

$R^3$ is selected from $NHR^5$ and $OR^5$;

$R^4$ is selected from H, $OR^5$, and $OC_{1-6}$-alkyl;

$R^6$ is selected from $C_{1-6}$-alkylene-$R^5$, cycloalkylene-$R^5$, heterocycloalkylene-$R^5$, arylene-$R^5$, and heteroarylene-$R^5$;

$R^7$ and $R^8$ are independently selected from H, $C_{1-6}$-alkylene-$R^5$, cycloalkylene-$R^5$, heterocycloalkylene-$R^5$, arylene-$R^5$, and heteroarylene-$R^5$;

wherein one of $R^5$ is -$L_n$-X, wherein L is a linker, n is selected from 0 and 1, and X is a chemical moiety that can be coupled with a targeting moiety, and wherein the remaining $R^5$ are H;

with (i) N,N'-disuccinimidyl carbonate (DSC), (ii) a thiocarbonylating reagent, particularly thiophosgene, 1,1'-thiocarbonyldiimidazole or 1,1'-thiocarbonyldi-2(1H)-pyridone; (iii) a iminocarbonylating reagent, particularly an isocyanide dichloride or phenylisotihocyanate; or (iv) an aldehyde, ketone or acyclic acetal.

EXAMPLES

Example 1 Synthesis of Amatoxin-Conjugation Molecules

1.1 Synthesis of 6'-N-Boc-(6-aminohexyl)-α-amanitin HDP 30.0132

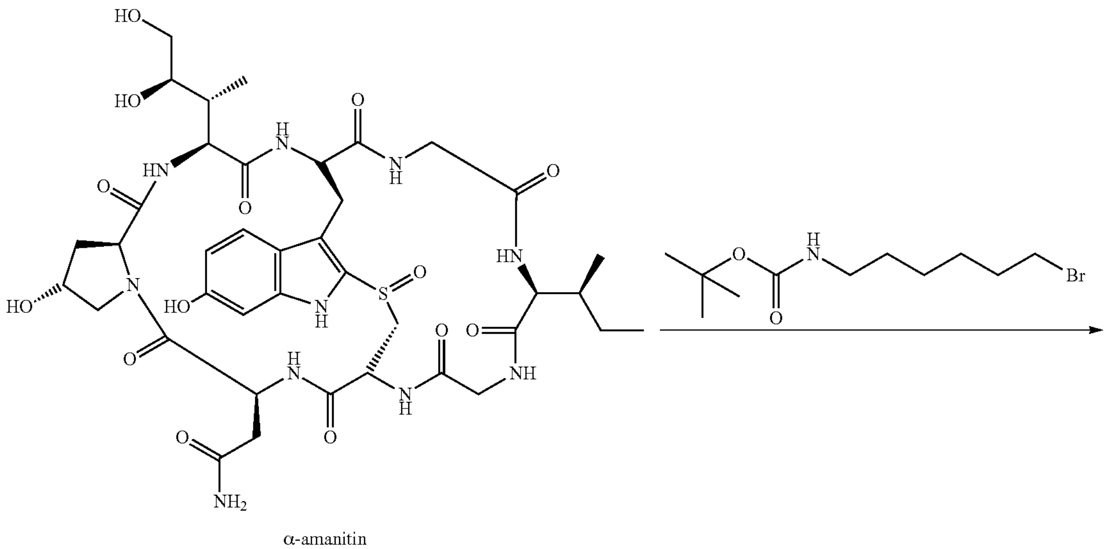

α-amanitin

-continued

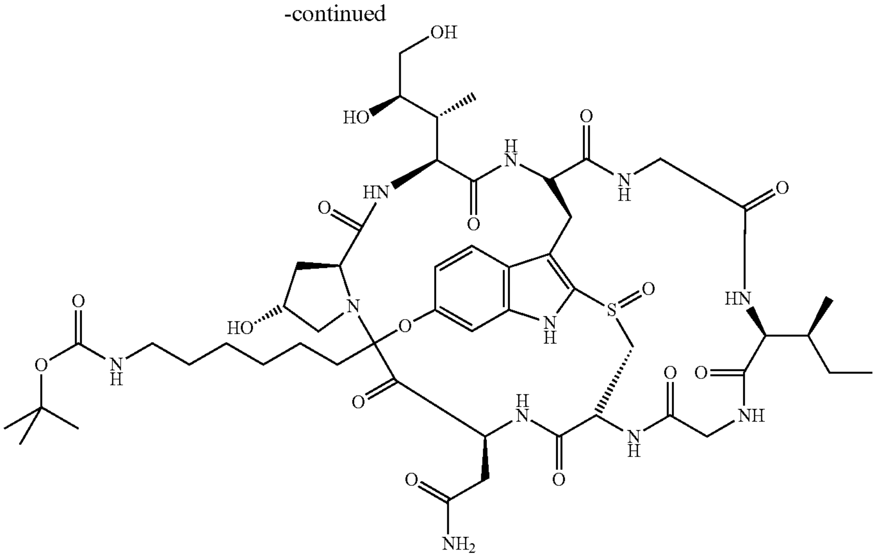

HDP 30.0132

Under argon and at room temperature 180 mg (196 μmol) of vacuum dried α-amanitin were dissolved in 5000 μl dry dimethyl sulfoxide (DMSO). N-Boc-aminohexylbromide (439 mg, 8 equivalents) and 1M sodium hydroxide (215.5 μl, 1.1 eq.) were added. After 2 h at room temperature the reaction mixture was acidified to pH=5 with 100 μl of a 1 M acetic acid solution in DMSO. Volatiles were evaporated in vacuum and the residue was dissolved in 500 μl methanol and added to 40 ml of ice cooled methyl tert-butyl ether (MTBE). The precipitate was centrifuged and washed by resuspension in 40 ml MTBE. The precipitate was and taken up in 4000 μl methanol filtered and purified in 500 μl portions by preparative HPLC on a C18 column (250×21.2 mm, Luna RP-18, 10 μm, 100 Å). Solvent A: water, solvent B: methanol; Gradient: 0 min 5% B; 5 min 5% B 20 min 100% B; 25 min 100% B; 27 min 5% B, 35 min 5% B; Flow 30 ml/min. The fractions with a retention time of 18.4-19.1 min were collected and the solvents evaporated to 126 mg (57%) HDP 30.0132 as a colorless solid.

MS (ESI+) 1118.5 $[M+H]^+$, 1140.5 $[M+Na]^+$

By evaporation of the fractions with a retention time of 12.8-13.4 min 35 mg (19%) of α-amanitin could be recovered.

1.2 Synthesis of 6'-(6-Aminohexyl)-α-amanitin HDP 30.0134

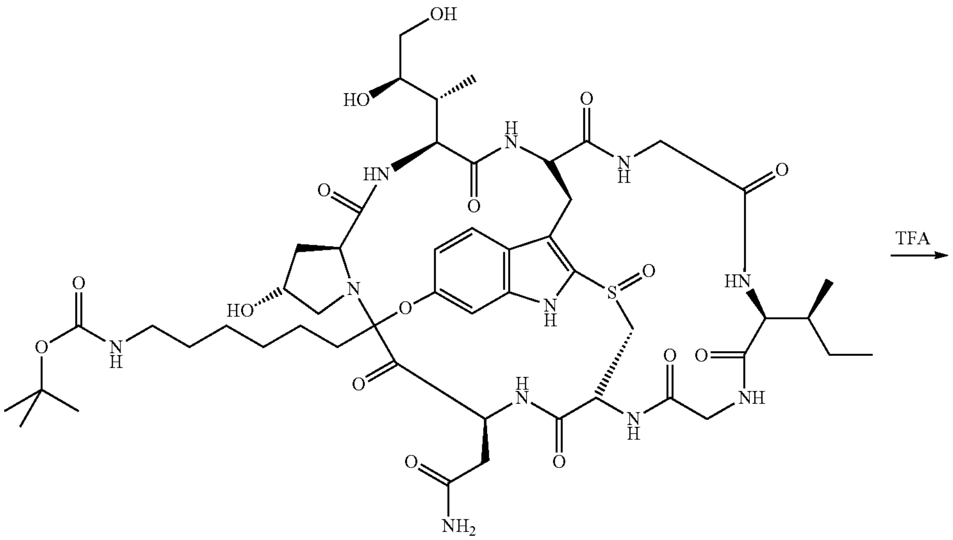

HDP 30.0132

-continued

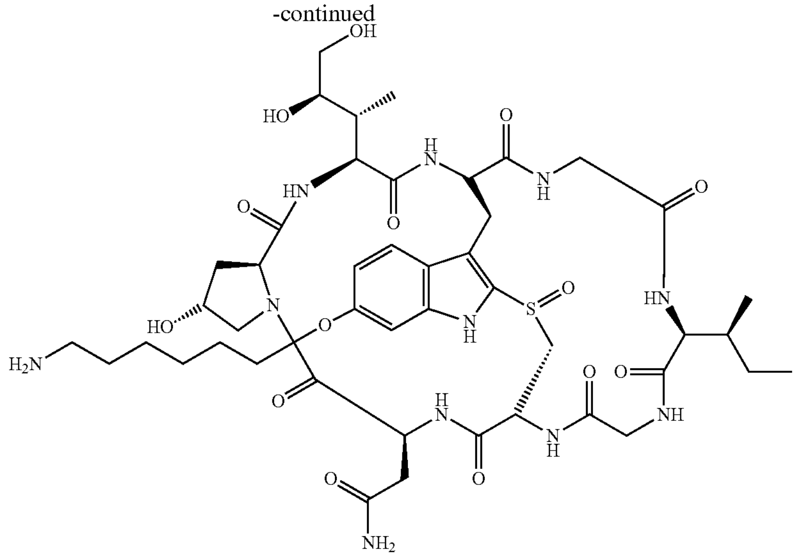

HDP 30.0134

6'-NH-boc-6-aminohexyl-α-amanitin (HDP 30.0132, 81.82 mg, 73.17 μmol) was dissolved in 300 μl trifluoroacetic acid (TFA). The reaction mixture was stirred under argon at ambient temperature. After 2 min the acid was removed in vacuo at 20° C. and traces of TFA are removed by co-evaporation with 2×3 ml dry toluene. The residue was dissolved in 3000 μl water/methanol 95:5 containing 0.05% TFA and purified in 500 μl portions by preparative HPLC on a C18 column (250×21.2 mm, Luna RP-18, 10 μm, 100 Å). Solvent A: water (containing 0.05% TFA), Solvent B: methanol (containing 0.05% TFA.) Gradient: 0 min 5% B; 5 min 5% B 20 min 100% B; 25 min 100% B; 27 min 5% B, 35 min 5% B; Flow 30 ml/min. The fraction with the retention time of 13.4-13.9 min was collected and the solvents evaporated to provide 75.52 mg (89%) HDP 30.0134 as a colorless solid.

HR-MS (ESI+) 1018.46749 calc. 1018.46679 for $C_{45}H_{68}N_{11}O_{14}S$ $[M+H]^+$ 1.3 Synthesis of 6'-(6-(Succinimidyloxy-carbonyl)-aminohexyl-α-amanitin HDP 30.0643

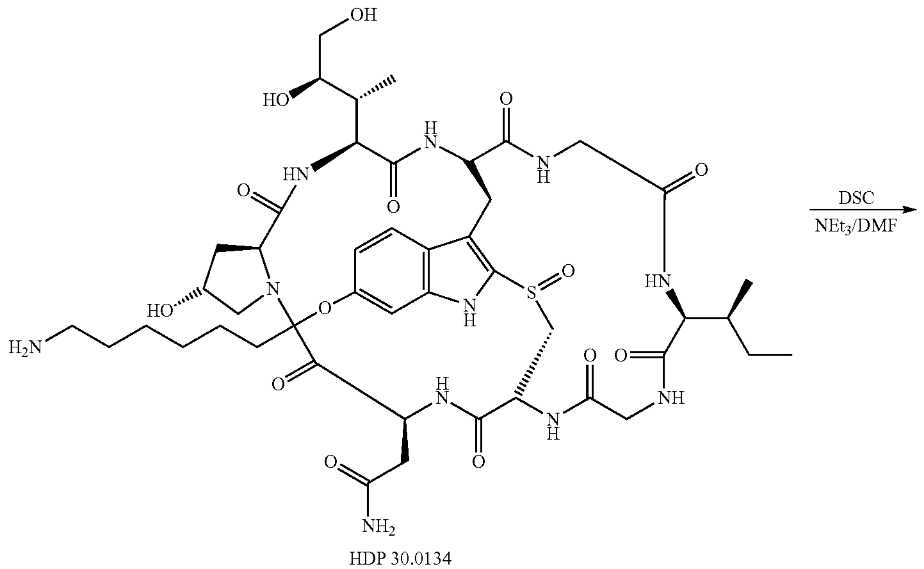

HDP 30.0134

-continued

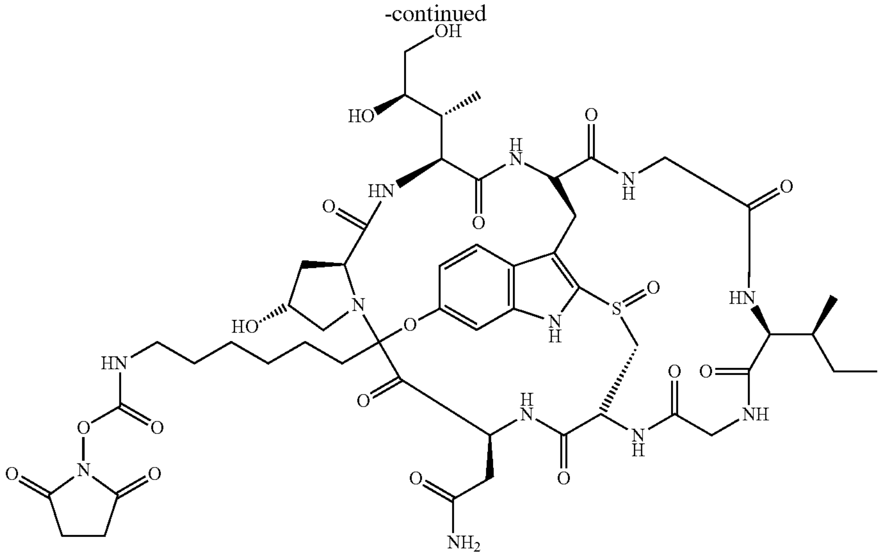

HDP 30.0643

HDP 30.0134 (160.52 mg, 141.78 μmol) was dissolved in 1000 μl dry dimethylformamide (DMF) and 363.19 mg (10 eq.) of N,N'-disuccinimidyl carbonate (DSC) in 4000 μl dry DMF were added at once, followed by 39.3 μl (2 eq.) triethylamine and the mixture was stirred at room temperature. After 30 min the reaction mixture was added drop wise in equal parts to two centrifugation tubes filled with 40 ml ice-cooled MTBE. The resulting precipitates were centrifuged and washed by resuspension in 40 ml MTBE each. The precipitates were dried in vacuo, dissolved and combined in 2400 μl 95% methanol containing 0.05% TFA and purified in portions of 400 μl by preparative HPLC on a C18 column (250×21.2 mm, Luna RP-18, 10 μm, 100 Å). Solvent A: water (containing 0.05% TFA). Solvent B: methanol (containing 0.05% TFA). Gradient: 0 min 5% B; 5 min 5% B 20 min 100% B; 25 min 100% B; 27 min 5% B, 35 min 5% B; Flow 30 ml/min. The fraction with the retention time of 15.4-16.5 min was collected and the solvents evaporated and the residue was lyophilized from 8 ml tert-butanol to 151.46 mg (92%) HDP 30.0643 as a white powder.

MS (ESI+) 1159.1 $[M+H]^+$, 1181.0 $[M+Na]^+$

1.4 Synthesis of Cyclic Carbonate Derivative HDP 30.1165

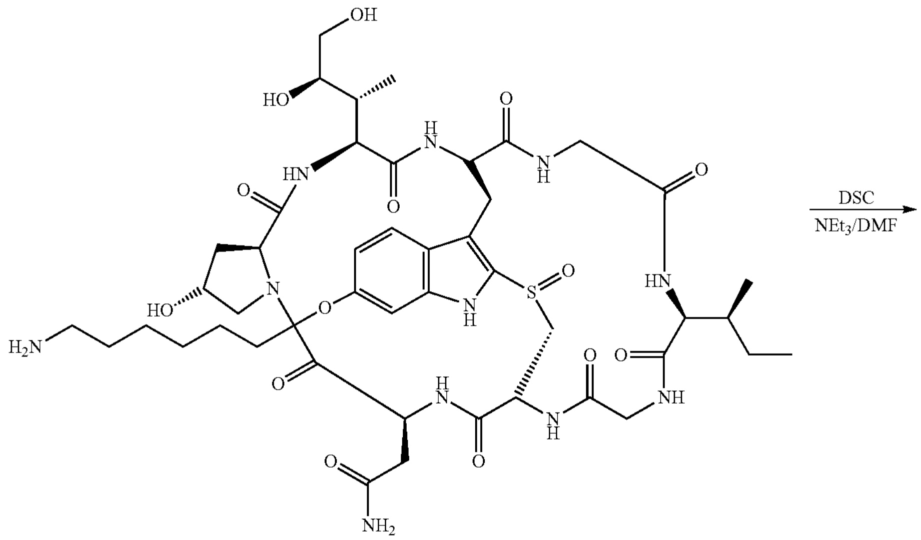

HDP 30.0134

-continued

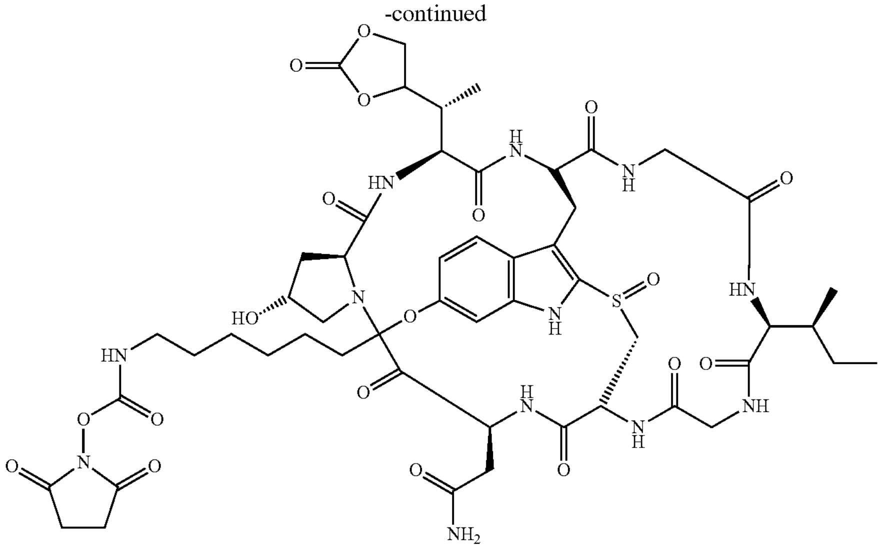

HDP 30.1165

10.23 mg (9.04 μmol) of HDP 30.0134 was dissolved in 500 μl dry dimethylformamide (DMF) and 452 μl (10 equivalents) of a 0.2 M solution of N,N'-disuccinimidyl carbonate (DSC) in dry DMF was added at once. Triethylamine (2.51 μl, 2 equivalents) were added and the mixture was stirred for 90 min at room temperature. Subsequently the volatiles were removed in vacuo at 40° C. bath temperature. The residue was dissolved in 500 μl 95% methanol containing 0.05% TFA and purified by preparative HPLC on a C18 column (250×21.2 mm, Luna RP-18, 10 μm, 100 Å). Solvent A: water (0.05% TFA). Solvent B: methanol (0.05% TFA). Gradient: 0 min 5% B; 5 min 5% B 20 min 100% B; 25 min 100% B; 27 min 5% B, 35 min 5% B; Flow 30 ml/min. The fraction with the retention time of 15.4-16.5 min was collected and the solvents evaporated and the residue was lyophilized from 2 ml tert-butanol to 9.06 mg (85%) HDP 30.1065 as a white powder.

MS (ESI+) 1185.10 $[M+H]^+$, 1207.07 $[M+Na]^+$ 1.5 Synthesis of 6'-N-Boc-(6-aminohexyl)-S-deoxy-α-amanitin HDP 30.0741

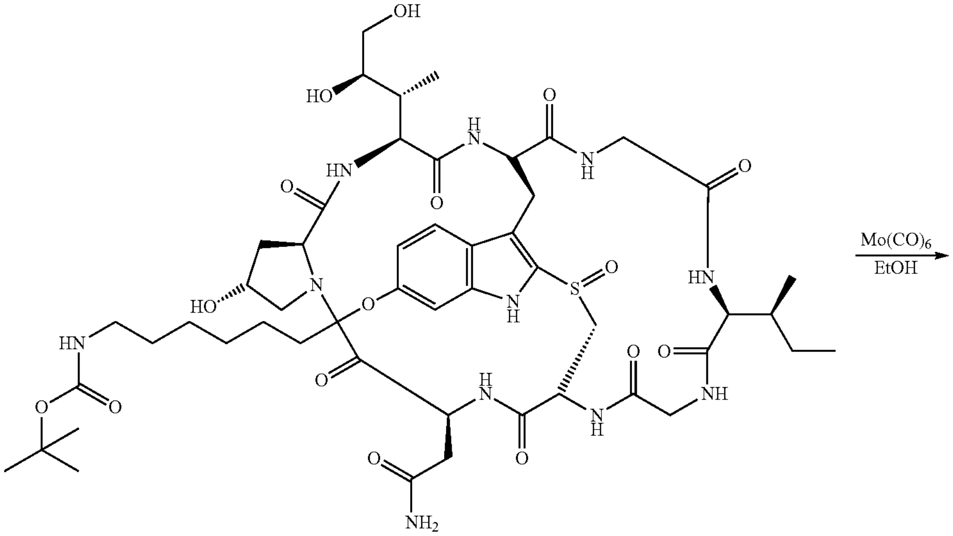

HDP 30.0132

-continued

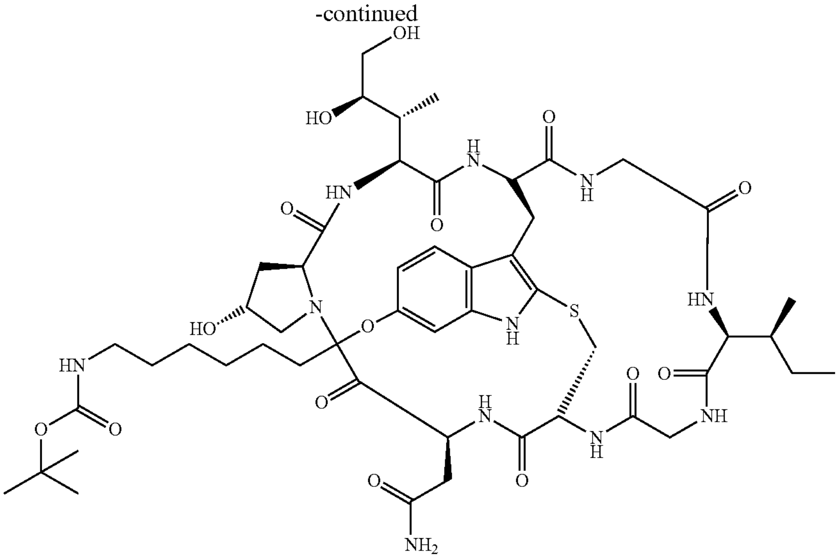

HDP 30.0741

To a solution of HDP 30.0132 (18.64 mg, 16.67 μmol) in 2 ml ethanol was added Molybdenumhexacarbonyl (51 mg, 11.6 equivalents) and the mixture was heated in a sealed tube to 75° C. for 25 h. Subsequently the volatiles were removed in vacuo and the residue is taken up in 2 ml methanol. Insoluble material is removed by centrifugation and the supernatant is concentrated to 500 μl and purified by preparative HPLC on a C18 column (250x21.2 mm, Luna RP-18, 10 μm, 100 Å). Solvent A: water, solvent B: methanol; Gradient: 0 min 5% B; 5 min 5% B 20 min 100% B; 25 min 100% B; 27 min 5% B, 35 min 5% B; Flow 30 ml/min. The fraction with the retention time of 17.9-18.6 min was collected and the solvents evaporated to 10.95 mg (60%) HDP 30.0741 as a colorless solid.

MS (ESI+) 1102.3 $[M+H]^+$, 1124.5 $[M+Na]^+$

1.6 Synthesis of 6'-(6-Aminohexyl)-S-deoxy-α-amanitin HDP 30.0743

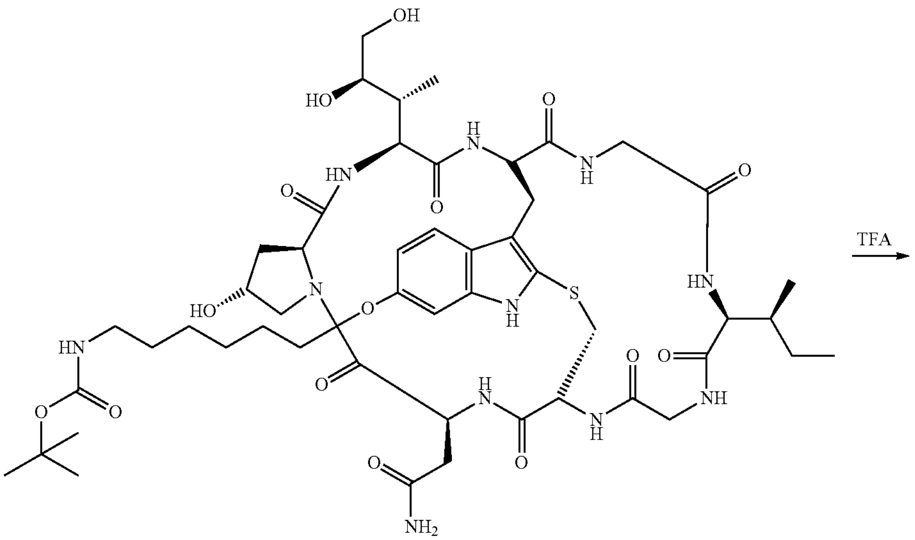

HDP 30.0741

-continued

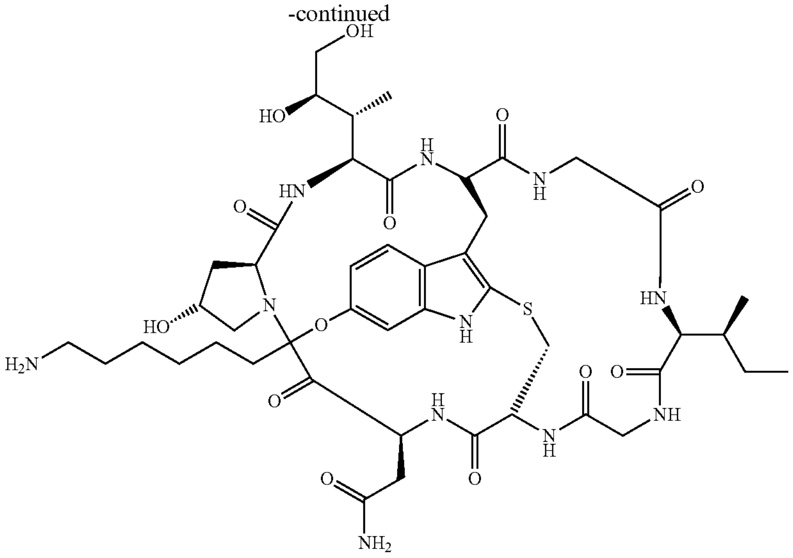

HDP 30.0743

HDP 30.0741 (10.95 mg, 9.93 μmol) was dissolved in 500 μl TFA and incubated for 2 min at room temperature. Then the volatiles are evaporated in vacuo and traces of TFA are removed by co-evaporation with 2×1 ml dry toluene. The 12.38 mg crude product is used in the next step without further purification.

MS (ESI+) 1002.4 $[M+H]^+$, 1024.3 $[M+Na]^+$

1.7 Synthesis of 6'-(6-(Succinimidyloxy-carbonyl)-aminohexyl-S-deoxy-α-amanitin HDP 30.1033

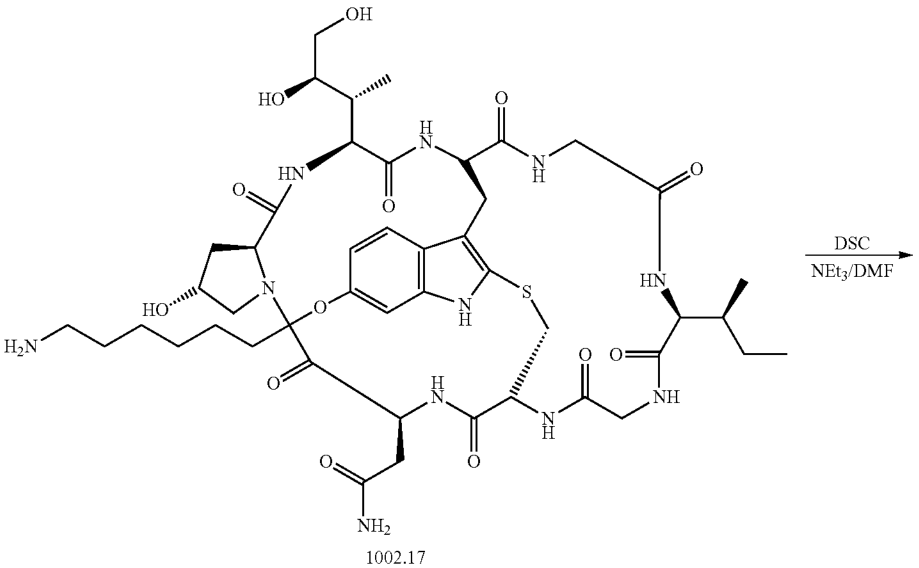

1002.17

$C_{45}H_{67}N_{11}O_{13}S$ + TFA = 1116, 19

-continued

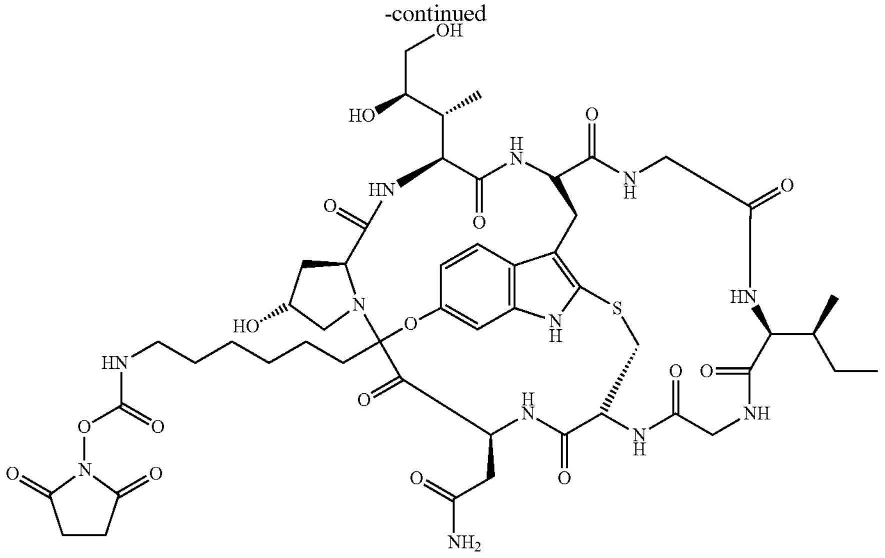

1143.25
$C_{50}H_{70}N_{12}O_{17}S$

HDP 30.0743 (12.38 mg, 10.51 μmol) was dissolved in 500 μl dry dimethylformamide (DMF) and 525 (10 eq.) of a 0.2N solution of N,N'-disuccinimidyl carbonate (DSC) in dry DMF were added at once, followed by 2.91 μl (2 eq.) triethylamine and the mixture was stirred at room temperature. After 30 min the reaction mixture was added drop wise in a centrifugation tube filled with 10 ml ice-cooled MTBE. The resulting precipitate was centrifuged and washed by resuspension in 10 ml MTBE each. The precipitate were dried in vacuo, dissolved in 500 μl 95% methanol containing 0.05% TFA and purified by preparative HPLC on a C18 column (250×21.2 mm, Luna RP-18, 10 μm, 100 Å). Solvent A: water (containing 0.05% TFA). Solvent B: methanol (containing 0.05% TFA). Gradient: 0 min 5% B; 5 min 5% B 20 min 100% B; 25 min 100% B; 27 min 5% B, 35 min 5% B; Flow 30 ml/min. The fraction with the retention time of 16.0-17.2 min was collected and the solvents evaporated and the residue was lyophilized from 3 ml tert-butanol to 10.93 mg (91%) HDP 30.1033 as a white powder

MS (ESI+) 1143.3 $[M+1-1]^+$ 1.8 Synthesis of Cyclic Carbonate Derivative HDP 30.1036

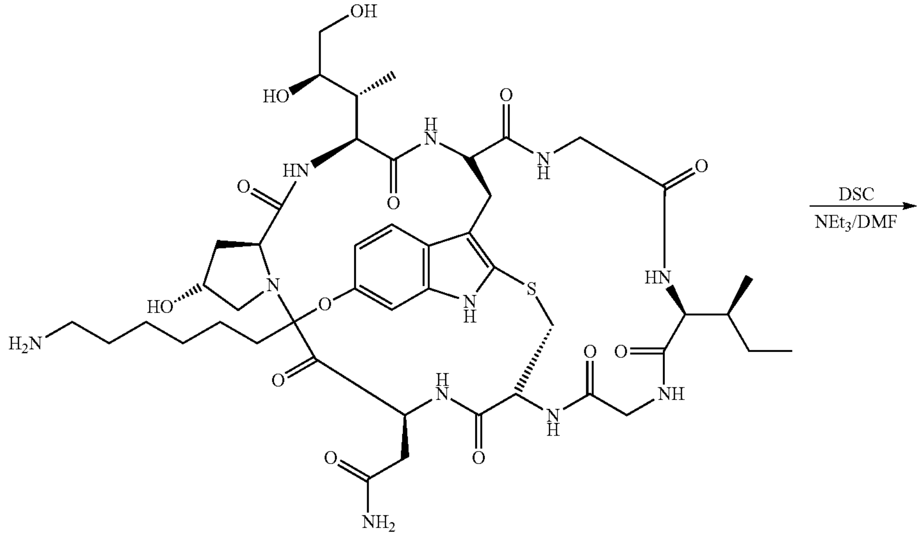

HDP 30.0743

-continued

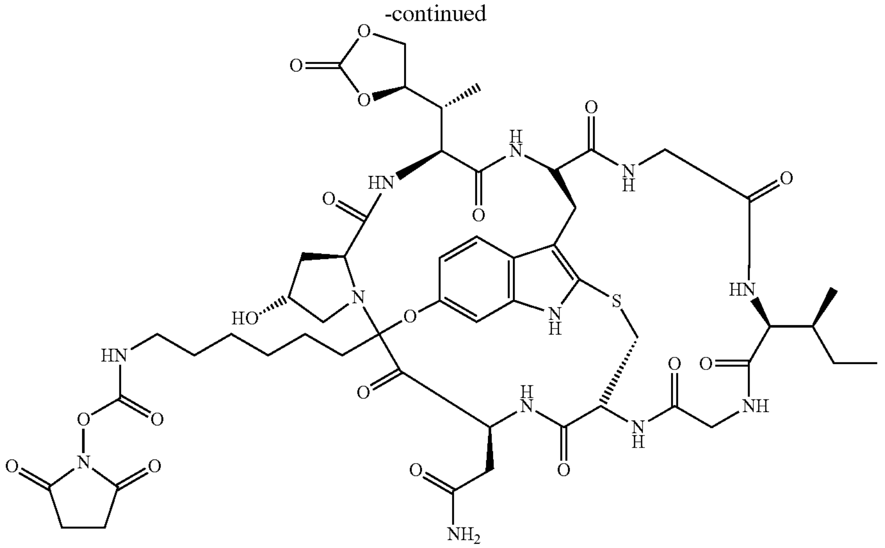

HDP 30.1036

Crude HDP 30.0743 (12.38 mg, 9.93 μmol) was dissolved in 500 μl dry dimethylformamide (DMF) and 497 μl (10 equivalents) of a 0.2 M solution of N,N'-disuccinimidyl carbonate in dry DMF was added at once. Triethylamine (2.75 μl, 2 equivalents) were added and the mixture was stirred for 90 min at room temperature. Subsequently the volatiles were removed in vacuo at 40° C. bath temperature. The residue was dissolved in 500 μl 95% methanol containing 0.05% TFA and purified by preparative HPLC on a C18 column (250×21.2 mm, Luna RP-18, 10 μm, 100 Å). Solvent A: water (0.05% TFA). Solvent B: methanol (0.05% TFA). Gradient: 0 min 5% B; 5 min 5% B 20 min 100% B; 25 min 100% B; 27 min 5% B, 35 min 5% B; Flow 30 ml/min. The fraction with the retention time of 15.9-17.2 min was collected and the solvents evaporated and the residue was lyophilized from 3 ml tert-butanol to 10.06 mg (87%) HDP 30.1036 as a white powder MS (ESI+) 1191.08 $[M+Na]^+$ Example 2 Synthesis of Amatoxin Antibody Conjugates—Conjugation of Trastuzumab with Pre-Activated Amatoxin-NHS-Carbamates 1.1 Trastuzumab-30.0643

1.15 mg mg preactivated amatoxin-linker derivative HDP 30.0643 were dissolved in 230 μl dry dimethylsulfoxide (DMSO) and added to 3.33 ml of Antibody solution 6 mg/ml in phosphate buffered saline (PBS, pH=7.4). The resulting solution was shaken at 4° C. overnight and separated by Sephadex G-25 gel filtration (PD-10 column; GE Healthcare Life Sciences). The PD-10 columns were prewashed with 6×5 ml PBS solutions, pH=7.4. The conjugate fractions were detected by Bradford solution and combined to one solution. The solution was then dialysed in a Slide-A-Lyzer cassette (Thermo Scientific; 0.5-3 ml; 20.000 MWCO) against 1 L PBS pH 7.4 overnight at 4° C. Protein concentration was determined by RotiQuant-Assay (Carl Roth; Germany). ADC concentration was increased in Amicon Ultra Centrifugal Filters 50'000 MWCO (Millipore; centrifugation at 4000 rpm) and finally adjusted to 3 mg/ml. Amanitin payload of Trastuzumab was determined by determination of UV absorption at A=280 nm and A=310 nm.

1.2 Trastuzumab-30.1033

2.00 mg preactivated amatoxin-linker derivative HDP 30.1033 were dissolved in 400 μl dry dimethylsulfoxide (DMSO) and added to 2.62 ml of Antibody solution 10 mg/ml in phosphate buffered saline (PBS, pH=7.4). The resulting solution was shaken at 4° C. overnight and separated by Sephadex G-25 gel filtration (PD-10 column; GE Healthcare Life Sciences). The PD-10 columns were prewashed with 6×5 ml PBS solutions, pH=7.4. The conjugate fractions were detected by Bradford solution and combined to one solution. The solution was then dialysed in a Slide-A-Lyzer cassette (Thermo Scientific; 0.5-3 ml; 20.000 MWCO) against 1 L PBS pH 7.4 overnight at 4° C. Protein concentration was determined by RotiQuant-Assay (Carl Roth; Germany). ADC concentration was increased in Amicon Ultra Centrifugal Filters 50'000 MWCO (Millipore; centrifugation at 4000 rpm) and finally adjusted to 3 mg/ml. Amanitin payload of Trastuzumab was determined by determination of UV absorption at A=280 nm and A=310 nm.

1.3 Trastuzumab-30.1036

2.00 mg preactivated amatoxin-linker derivative HDP 30.1036 were dissolved in 400 μl dry dimethylsulfoxide (DMSO) and added to 2.57 ml of Antibody solution 10 mg/ml in phosphate buffered saline (PBS, pH=7.4). The resulting solution was shaken at 4° C. overnight and separated by Sephadex G-25 gel filtration (PD-10 column; GE Healthcare Life Sciences). The PD-10 columns were prewashed with 6×5 ml PBS solutions, pH=7.4. The conjugate fractions were detected by Bradford solution and combined to one solution. The solution was then dialysed in a Slide-A-Lyzer cassette (Thermo Scientific; 0.5-3 ml; 20.000 MWCO) against 1 L PBS pH 7.4 overnight at 4° C. Protein concentration was determined by RotiQuant-Assay (Carl Roth; Germany). ADC concentration was increased in Amicon Ultra Centrifugal Filters 50'000 MWCO (Millipore; centrifugation at 4000 rpm) and finally adjusted to 3 mg/ml.

Amanitin payload of Trastuzumab was determined by determination of UV absorption at A=280 nm and A=310 nm.

1.4 Trastuzumab-30.1165

0.90 mg preactivated amatoxin-linker derivative HDP 30.1165 were dissolved in 180 μl dry dimethylsulfoxide (DMSO) and added to 2.00 ml of Antibody solution 5 mg/ml in phosphate buffered saline (PBS, pH=7.4). The resulting solution was shaken at 4° C. overnight and separated by Sephadex G-25 gel filtration (PD-10 column; GE Healthcare Life Sciences). The PD-10 columns were prewashed with 6×5 ml PBS solutions, pH=7.4. The conjugate fractions were detected by Bradford solution and combined to one solution. The solution was then dialysed in a Slide-A-Lyzer cassette (Thermo Scientific; 0.5-3 ml; 20.000 MWCO) against 1 L PBS pH 7.4 overnight at 4° C. Protein concentration was determined by RotiQuant-Assay (Carl Roth; Germany). ADC concentration was increased in Amicon Ultra Centrifugal Filters 50'000 MWCO (Millipore; centrifugation at 4000 rpm) and finally adjusted to 3 mg/ml. Amanitin payload of Trastuzumab was determined by determination of UV absorption at A=280 nm and A=310 nm.

| Antibody | Toxin linker derivative | conjugate | payload |
|---|---|---|---|
| Trastuzumab | HDP 30.1036 | Her-30.1036 | 4.0 |
| Trastuzumab | HDP 30.0643 | Her-30.0643 | 4.4 |
| Trastuzumab | HDP 30.1165 | Her-30.1165 | 5.0 |
| Trastuzumab | HDP 30.1033 | Her-30.1033 | 3.9 |

Example 3 Cytotoxicity of Her-30.0643 [4.4], Her-30.1033 [3.9], Her-30.1036 [4.0] and Her-30.1165 [5.0] on HER2-Positive Tumor Cell Lines In Vitro Cytotoxic activity of Trastuzumab-amatoxin conjugates was evaluated in vitro with the HER2-positive tumor cell lines SK-OV-3 (ovar), SKBR-3 (breast) and JIMT-1 (breast) and the chemiluminescent BrdU incorporation assay (Roche Diagnostics). Cell viability was determined after 72 h incubation with different concentrations of conjugates at 37° C. and 5% $CO_2$ by measurement of fixed and permeabilized cells with an anti-BrdU-HRP antibody in a BMG Labtech Optima microplate reader. $EC_{50}$ value of dose-response curve was calculated by Graphpad Prism 4.0 software.

$EC_{50}$ values of the Trastuzumab-amatoxin conjugates in different Her2 positive cell lines (see also FIGS. 2 to 5):

| Conjugate | SKOV-3 | SKBR-3 | JIMT-1 |
|---|---|---|---|
| Her-30.1036 [4.0] | $3.8 \times 10^{-11}$M | $3.3 \times 10^{-11}$M | $2.1 \times 10^{-9}$M |
| Her-30.0643 [4.4] | $2.9 \times 10^{-11}$M | $2.0 \times 10^{-11}$M | $1.0 \times 10^{-9}$M |
| Her-30.1165 [5.0] | $1.1 \times 10^{-10}$M | — | — |
| Her-30.1033 [3.9] | $2.7 \times 10^{-11}$M | $1.3 \times 10^{-11}$M | $7.9 \times 10^{-9}$M |

Figure 6:
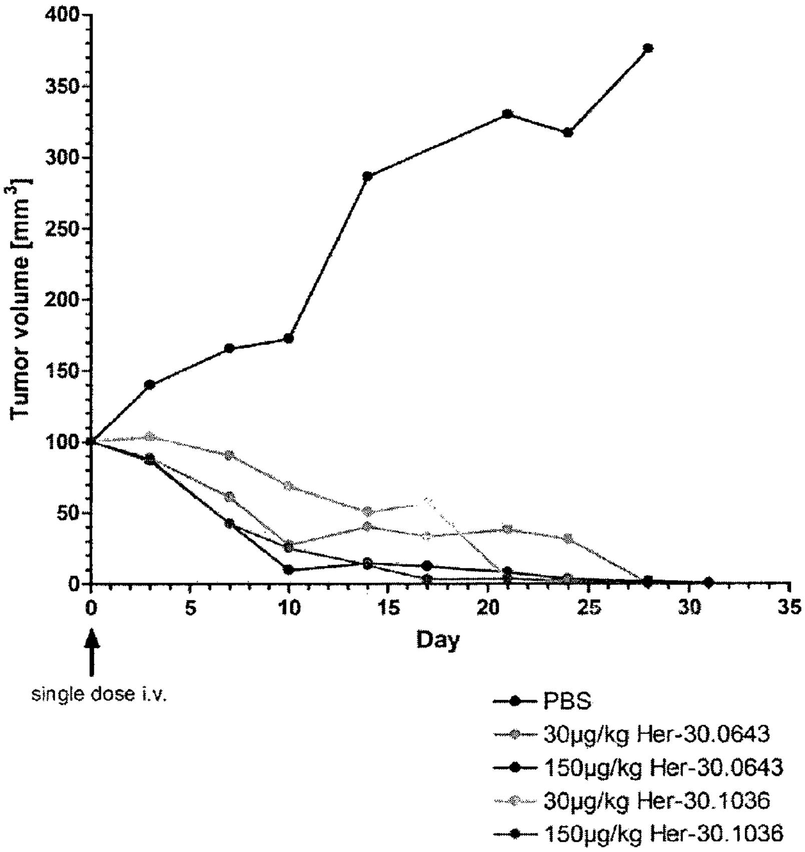
FIG. 6 shows the in vivo efficacy of two different amatoxin amatoxin-Trastuzumab conjugates in a JIMT-1 breast cancer xenograft model.

Example 4 In Vivo Efficacy of her-30.0643 [4.4] and her-30.1036 [4.0] in the Trastuzumab-Resistant JIMT-1 Xenograft Model Six-week old intact female NMRI nu/nu athymic mice were purchased (Janvier) and randomly divided into three groups of eight mice each. $5\times10^6$ JIMT-1 cells were injected s.c. into the flank of each mouse. The Trastuzumab-Amatoxin conjugates Her-30.0643 [4.4] and Her-30.1036 [4.0] were injected once i.v. at a dose of 30 μg/kg and 150 μg/kg with respect to amanitin at day 14 after tumor inoculation, whereas the negative control was injected with vehicle (PBS buffer). The tumour volume was recorded (see FIG. 6). Both conjugates showed high antitumoral activity resulting in complete tumor reduction at 30 μg and 150 μg/kg.

Example 5 Tolerability of her-30.0643 [4.4] and her-30.1036 [4.0] in Mice

Figure 7:
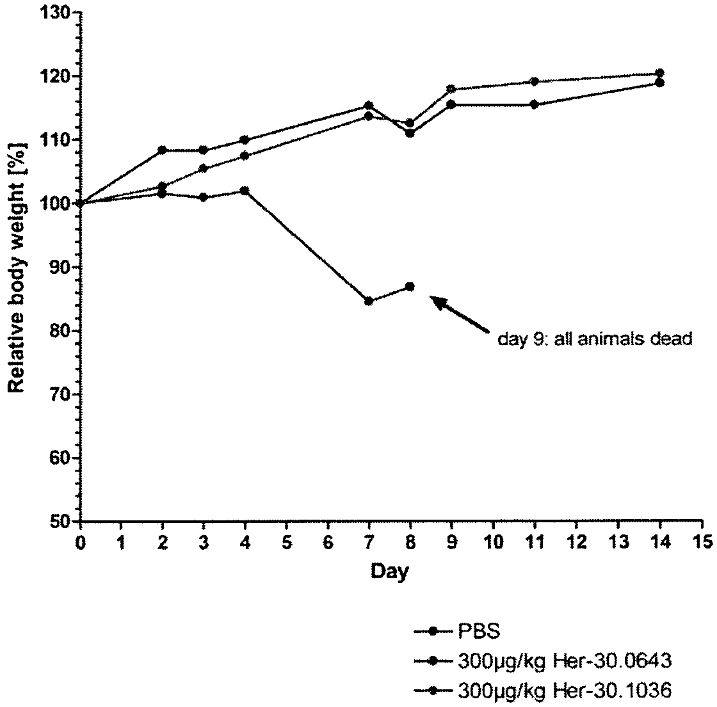
FIG. 7 shows the in vivo tolerability of two different amatoxin amatoxin-Trastuzumab conjugates in female NMRI nu/nu mice.

Seven-week old intact female NMRI nu/nu athymic mice were purchased (Janvier) and randomly divided into three groups of three mice per group. The Herceptin-Amatoxin conjugates Her-30.0643 [4.4] and Her-30.1036 [4.0] were injected once i.v. at a dose of 300 μg/kg, whereas the negative control was injected with vehicle (PBS buffer). The weight of the mice was recorded (see FIG. 7). All animals treated with Her-30.0643 [4.4] died within nine days after application, whereas all animals treated with Her-30.1036 [4.0] showed body weights comparable to the negative control group after day 14.

We claim:

1. An amatoxin of Formula I

I

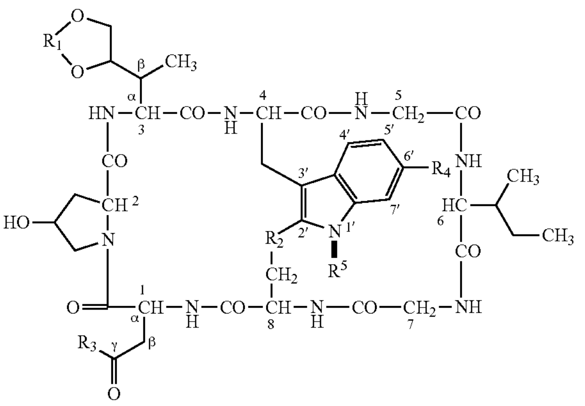

wherein:

$R^1$ is selected from C═O, C═S, C═$NR^6$ and $CR^7R^8$;

$R^2$ is selected from S═O, $SO_2$, and S;

$R^3$ is selected from $NHR^5$ and $OR^5$;

$R^4$ is selected from H, $OR^5$, and $OC_{1-6}$-alkyl;

$R^6$ is selected from $C_{1-6}$-alkylene-$R^5$, cycloalkylene-$R^5$, heterocycloalkylene-$R^5$, arylene-$R^5$, and heteroarylene-$R^5$;

$R^7$ and $R^8$ are independently selected from H, $C_{1-6}$-alkylene-$R^5$, cycloalkylene-$R^5$, heterocycloalkylene-$R^5$, arylene-$R^5$, and heteroarylene-$R^5$;

wherein:

(i) each $R^5$ is H;

(ii) one of $R^5$ is -$L_n$-X, wherein L is a linker, n is selected from 0 and 1, and X is a chemical moiety that can be coupled with a targeting moiety, and wherein the remaining $R^5$ are H; or (iii) one of $R^5$ is -$L_n$-X*—Y, wherein L is a linker, n is selected from 0 and 1, Y is a targeting moiety, and X* is a chemical moiety resulting from coupling X with a functional group of Y, and wherein the remaining $R^5$ are H and wherein the targeting moiety is a moiety selected from the group of:

(a) antibodies or antigen-binding fragments thereof;

(b) antibody-like proteins that are engineered proteins that bind to a target molecule and comprise at least one variable peptide loop attached at both ends to a protein scaffold; and (c) nucleic acid aptamers.

2. The amatoxin of claim 1, wherein said functional group of Y is an amino group.

3. The amatoxin of claim 2, wherein X* is a urea moiety.

4. The amatoxin of claim 1, wherein said residue $R^5$ being $-L_n-X^*-Y$ is:

(i) present in $R^1$;

(ii) present in $R^3$;

(iii) present in $R^4$; or (iv) attached to the nitrogen atom of the tryptophan moiety.

5. The amatoxin of claim 1, wherein n is 1, and wherein the linker has a length of up to 12 atoms.

6. The amatoxin of claim 1, wherein the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

7. The amatoxin of claim 1, wherein the linker L comprises a moiety selected from one of the following moieties: a disulfide, an ether, a thioether, an amine, an ester, a carboxamide, a urethane, and a urea moiety.

8. The amatoxin of claim 1, wherein the targeting moiety specifically binds to an epitope that is present on a tumour cell.

9. The amatoxin of claim 1, wherein the antibody or the antigen-binding fragment thereof is selected from a diabody, a tetrabody, a nanobody, a chimeric antibody, a deimmunized antibody, a humanized antibody or a human antibody.

10. The amatoxin of claim 1, wherein the antigen binding fragment is selected from the group of Fab, $F(ab')_2$, Fd, Fv, single-chain Fv, and disulfide-linked Fvs (dsFv).

11. The amatoxin of claim 1, for use as a medicament.

12. The amatoxin of claim 1, for use in the treatment of cancer in a patient.

13. Pharmaceutical composition comprising the amatoxin according to claim 1, and further comprising one or more pharmaceutically acceptable diluents, carriers, excipients, fillers, binders, lubricants, glidants, disintegrants, adsorbents; and/or preservatives.

14. The amatoxin of claim 1, wherein X is a carbamic acid derivative —NH—C(O)—Z, wherein Z is a leaving group that can be replaced by a nucleophilic group of a targeting moiety.

15. The amatoxin of claim 14, wherein Z is selected from: -$^t$butyloxy, -succinimidyloxy, -1-O-succinimidyloxy-3-sulfonate (-Sulfo-NHS), —O-(4-nitrophenyloxy), —O-(3-nitrophenyloxy), dinitrophenyloxy), —O-(2,4-dichloro-6-nitrophenyloxy), -pentafluorophenyloxy, -pentachlorophenyloxy, —O-(2,4,5-trichlorophenyloxy), —O-(3,4-dihydro-3-hydroxy-4-oxo-1,2,3-benzotriazine-3-yl), —O-(endo-1-hydroxy-5-norbornene-2,3-dicarboximide-1-yl), -1-phthalimidoyloxy, -1-benzotriazolyloxy, -1-(7-aza-benzotriazolyl)oxy,), and —N-imidazolyl.

16. A method for synthesizing the amatoxin of claim 14, comprising the step of reacting the dihydroxyisoleucine moiety of an amatoxin of Formula II

II

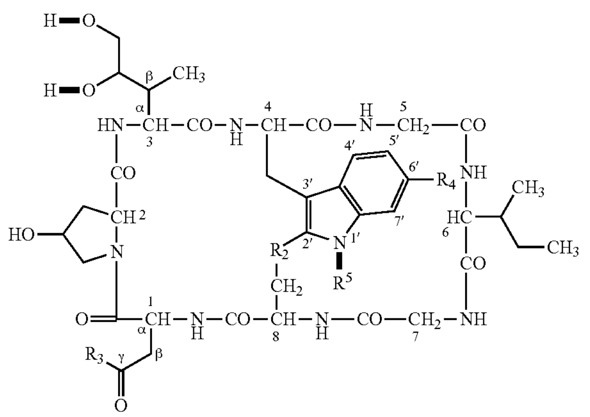

wherein:

$R^2$ is selected from S═O, $SO_2$, and S;

$R^3$ is selected from $NHR^5$ and $OR^5$;

$R^4$ is selected from H, $OR^5$, and $OC_{1-6}$-alkyl;

$R^6$ is selected from $C_{1-6}$-alkylene-$R^5$, cycloalkylene-$R^5$, heterocycloalkylene-$R^5$, arylene-$R^5$, and heteroarylene-$R^5$;

$R^7$ and $R^8$ are independently selected from H, $C_{1-6}$-alkylene-$R^5$, cycloalkylene-$R^5$, heterocycloalkylene-$R^5$, arylene-$R^5$, and heteroarylene-$R^5$;

wherein one of $R^5$ is $-L_n-X$, wherein L is a linker, n is selected from 0 and 1, and X is a chemical moiety that can be coupled with a targeting moiety, and wherein the remaining $R^5$ are H;

with (i) N,N'-disuccinimidyl carbonate (DSC), (ii) a thiocarbonylating reagent, (iii) an iminocarbonylating reagent, or (iv) an aldehyde, ketone or acyclic acetal; wherein the reaction of said dihydroxyisoleucine moiety with a reagent according to (i), (ii), (iii) or (iv) results in the formation of the cyclic structure

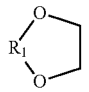

according to Formula I.

17. The amatoxin of claim 1, wherein n is 1, and wherein the linker has a length of from 2 to 10 atoms.

18. The amatoxin of claim 1, wherein n is 1, and wherein the linker has a length of from 4 to 9 atoms.

19. The amatoxin of claim 1, wherein n is 1, and wherein the linker has a length of from 6 to 8 atoms.

20. The amatoxin of claim 1, wherein the targeting moiety specifically binds to an epitope of human epidermal growth factor receptor 2 (HER2).

21. The amatoxin of claim 1, for use in the treatment of cancer in a patient, wherein the cancer is selected from the group of breast cancer, pancreatic cancer, cholangiocarcinoma, colorectal cancer, lung cancer, prostate cancer, ovarian cancer, stomach cancer, kidney cancer, malignant melanoma, leukemia, and malignant lymphoma.

22. The amatoxin of claim 1, wherein (a) the antibodies are selected from the group of antibodies of subtypes IgG, IgE, IgM, IgD, IgA and IgY, classes IgG1, IgG2, IgG3, IgG4, IgA1, IgA2 and anti-idiotypic antibodies; (b) the antibody fragments are selected from single chain antibodies, Fab fragments, F(ab')2 fragments, diabodies, tetrabodies, nanobodies, and epitope-binding fragments of any of the antibodies of (a) above; or (c) the antibody-like proteins are selected from the group of affibodies, anticalins, and designed ankyrin repeat proteins.

23. The amatoxin of claim 14, the nucleophilic group of the targeting moiety is a primary amine of the targeting moiety.

24. The method of claim 16, wherein the thiocarbonylating reagent is thiophosgene, 1,1'-thiocarbonyldiimidazole or 1,1'-thiocarbonyldi-2(1H)-pyridone and the iminocarbonylating reagent is an isocyanide dichloride or phenylisothiocyanate.

* * * * *